United States Patent [19]
Bru-Magniez et al.

[11] Patent Number: 5,231,094
[45] Date of Patent: Jul. 27, 1993

[54] TRIAZOLOPYRIMIDINES WHICH ARE ANGIOTENSIN II RECEPTOR ANTAGONISTS AND PHARMACEUTICAL COMPOSITIONS IN WHICH THEY ARE PRESENT

[75] Inventors: Nicole Bru-Magniez, Paris; Timur Güngor, Rueil Malmaison; Jean-Marie Teulon, La Celle Saint Cloud, all of France

[73] Assignee: Societe Anonyme: Laboratoires UPSA, Agen, France

[21] Appl. No.: 863,955

[22] Filed: Apr. 6, 1992

[30] Foreign Application Priority Data

Feb. 24, 1992 [FR] France .................. 92 02109

[51] Int. Cl.$^5$ ........................... C07D 487/04
[52] U.S. Cl. .................. 514/233.2; 514/253; 514/258; 544/117; 544/118; 544/263; 544/281; 544/309; 544/320; 548/253; 558/303; 560/179
[58] Field of Search ............ 544/118, 263, 281; 514/233.2, 258, 253

[56] References Cited

U.S. PATENT DOCUMENTS

| | | | |
|---|---|---|---|
| 4,483,987 | 11/1984 | Wagner et al. | 544/263 |
| 4,567,263 | 1/1986 | Eicken et al. | 544/281 |
| 4,576,943 | 3/1988 | Tomcufcik | 514/233.2 |
| 4,895,850 | 1/1990 | Gesing | 514/258 |
| 5,100,897 | 3/1992 | Allen et al. | 514/269 |
| 5,102,880 | 4/1992 | Chakravarty et al. | 514/112 |
| 5,127,936 | 6/1992 | Selby | 544/263 |

OTHER PUBLICATIONS

Herold et al. Chem. Abst. vol. 115, Entry 159173y (1991) abstracting EP 435827.
Herold et al. Chem. Abst. vol. 114 Entry 247301y (1991) abstracting EP407342.

*Primary Examiner*—Donald G. Daus
*Attorney, Agent, or Firm*—Rosen, Dainow & Jacobs

[57] ABSTRACT

The present invention relates to the derivatives of the formula

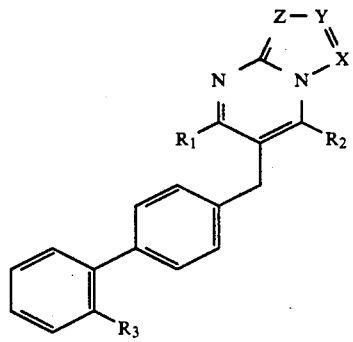

and their tautomeric forms, as well as their addition salts, and to their use in therapeutics, especially for the treatment of cardiovascular diseases and in particular for the treatment of hypertension, cardiac insufficiency and diseases of the arterial wall.

10 Claims, No Drawings

TRIAZOLOPYRIMIDINES WHICH ARE ANGIOTENSIN II RECEPTOR ANTAGONISTS AND PHARMACEUTICAL COMPOSITIONS IN WHICH THEY ARE PRESENT

The present invention relates, by way of novel products, to the polyazaindene derivatives of general formula (I) below and their tautomeric forms and, if appropriate, their addition salts, in particular the pharmaceutically acceptable addition salts.

The compounds in question have a very valuable pharmacological profile insofar as they possess antagonistic properties towards angiotensin II receptors. They are therefore particularly indicated for the treatment of cardiovascular diseases and in particular for the treatment of hypertension, for the treatment of cardiac insufficiency and for the treatment of diseases of the arterial wall.

The present invention further relates to the method of preparing said products and to their uses in therapeutics.

These polyazaindene derivatives and their tautomeric forms have general formula (I):

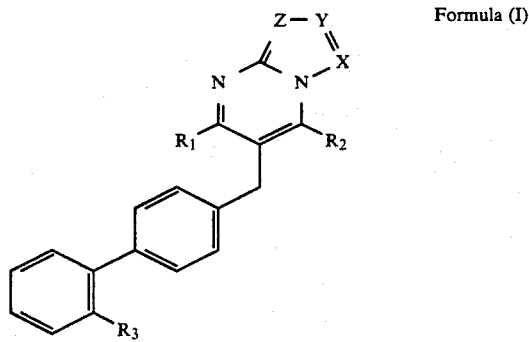

Formula (I)

In formula (I) one of the radicals $R_1$ and $R_2$ is a lower alkyl radical having 1 to 6 carbon atoms and the other is the hydrogen atom, a halogen atom or a group $OR_4$, $SR_4$,

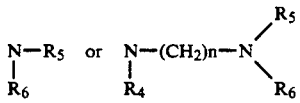

in which:

$R_4$ is the hydrogen atom, a lower alkyl radical having 1 to 6 carbon atoms or a $C_3$–$C_7$ cycloalkyl radical, $R_5$ and $R_6$, which are identical or different, are a hydrogen atom, a lower alkyl having 1 to 6 carbon atoms or a $C_3$–$C_7$ cycloalkyl radical, or they form, together with the nitrogen atom to which they are attached, a 5- to 7-membered ring which can contain 1 to 3 heteroatoms selected from oxygen, sulfur or nitrogen, and n is an integer from 1 to 4;

X, Y and Z, which are identical or different, are the nitrogen atom, a group C-$R_7$, in which $R_7$ is a hydrogen or halogen atom, a lower alkyl radical having 1 to 6 carbon atoms or a $C_3$–$C_7$ cycloalkyl radical, or else a group $OR_4$, $SR_4$,

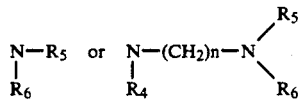

$R_4$, $R_5$, $R_6$ and n being as defined above, at least one of X, Y and Z being the nitrogen atom; and $R_3$ is an acid group or a tetrazole group.

The above-mentioned derivatives must also be considered in their tautomeric form.

The above-mentioned derivatives can take the form of addition salts, in particular the pharmaceutically acceptable addition salts.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

$C_3$–$C_7$ cycloalkyl radical is understood as meaning a saturated cyclic hydrocarbon radical, preferably a cyclopropane, cyclobutane, cyclohexane or cycloheptane radical.

Halogen is understood as meaning a chlorine, bromine, iodine or fluorine atom.

A 5- to 7-membered ring which can contain 1 to 3 heteroatoms selected from oxygen, sulfur or nitrogen is preferably a heterocycle selected from morpholine, piperazine, piperidine, pyrrolidine or imidazoline.

The invention relates in particular to the derivatives of general formula (I) in which: one of the radicals $R_1$ and $R_2$ is a lower alkyl radical having 1 to 6 carbon atoms and the other is a halogen atom, a hydroxyl or amino group or a group —$NR_5R_6$ or NH—$(CH_2)_n$—$NR_5R_6$ in which $R_5$ and $R_6$ form, together with the nitrogen atom to which they are attached, a heterocycle selected from the group comprising morpholine, piperazine, piperidine, pyrrolidine and imidazolidine and n is an integer from 1 to 4, preferably equal to 2; X, Y and Z, which are identical or different, are the nitrogen atom or a group C-$R_7$ in which $R_7$ is the hydrogen atom or a lower alkyl radical having 1 to 6 carbon atoms, at least one of X, Y and Z being the nitrogen atom; and $R_3$ is a tetrazolyl group.

According to one embodiment, $R_1$ is an n-propyl group.

According to one embodiment, $R_2$ is a hydroxyl group.

According to another embodiment, $R_2$ is the morpholino group.

According to another embodiment, $R_2$ is the morpholinoethylamino group.

According to one embodiment, X is the nitrogen atom.

According to one embodiment, Y is the nitrogen atom.

According to another embodiment, Y is the C—$CH_3$ group.

According to yet another embodiment, Z is the nitrogen atom.

According to another embodiment, Z is the CH group.

According to one embodiment, $R_3$ is a tetrazol-5-yl group.

The particularly preferred compounds of the invention are selected from the products of the formulae

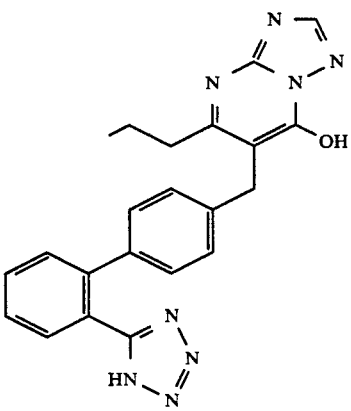

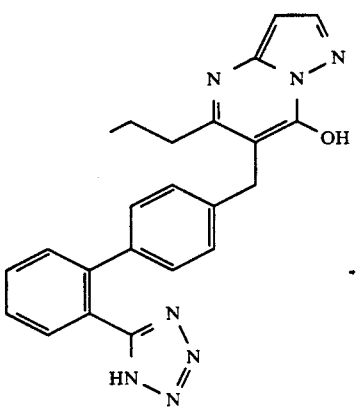

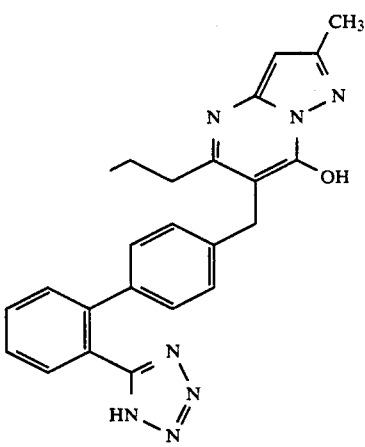

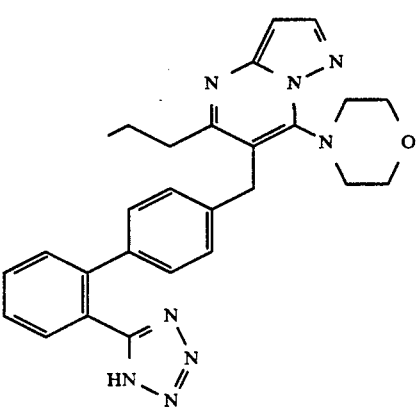

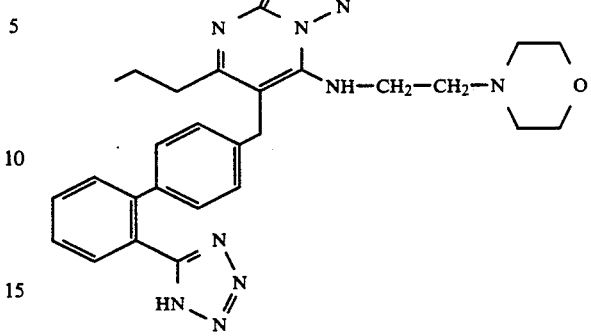

According to the invention it will be possible to synthesize the compounds of formula (I) in accordance with the following reaction sequence:

Methods known per se, such as, for example, the Claisen reaction or the method using Meldrum's acid, which methods can be found in the following literature references:

OIKAWA Y.; SUGANO K.; YONEMITSU O.; J. Org. Chem., 1978, 43(10), 2087-88,

WIERENGA W.; SKULNICK H. I.; J. Org. Chem., 1979, 44, 310,

HOUGHTON R.; LAPHAM D.; SYNTHESIS, 1982, 6, 451-2,

BRAM G.; VILKAS M.; Bull. Soc. Chim. France, 1964(5), 945-51,

BALYAKINA M. V.; ZHDANOVICH E. S.; PREOBRAZHENSKII N. A.; Tr. Vses. Nauchn. Issled. Vitam in. Inst., 1961, 7, 8-16, RENARD M.; MAQUINAY A.; Bull. Soc. Chim. Belg., 1946, 55, 98-105, BRUCE F. W.; COOVER H. W.; J. Am. Chem. Soc., 1944, 66. 2092-94, and EBY C. J. and HAUSER C. R.; J. Am. Chem. Soc., 1957, 79, 723-5, will be used to prepare the alkyl 3-aoxoalkanoates of formula (II):

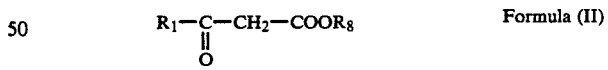
Formula (II)

in which $R_1$ is as defined above and $R_8$ is a lower alkyl radical, preferably methyl or ethyl.

The compounds of the formula

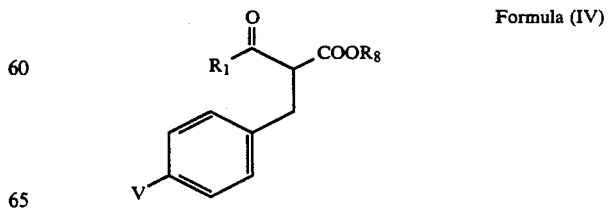
Formula (IV)

will be obtained by benzylating the compounds of formula (II) with compounds of formula (III):

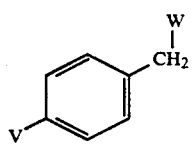

Formula (III)

in the presence of a base such as sodium or potassium carbonate in acetone, a sodium or potassium alcoholate in an alcohol, or sodium or lithium hydride in solvents such as tetrahydrofuran, dioxane or dimethylformamide, for example, at a temperature of between 50° and 100° C., or else in the presence of one equivalent of lithium chloride or bromide and two equivalents of diisopropylethylamine in tetrahydrofuran under reflux, according to the following reference:

SUNG-EUN YOO; KYU YANG YI; Bull. Korean Chem. Soc., 1989, 10(1), 112.

These compounds of formula (IV) can also be obtained by condensation of an aldehyde of the formula

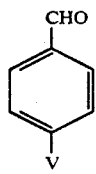

Formula (V)

with the compounds of formula (II), followed by hydrogenation in the presence of a catalyst such as Raney nickel, palladium-on-charcoal or platinum oxide, in a solvent such as an alcohol or tetrahydrofuran, under pressure or at ordinary pressure if the substituents present allow it.

In more general terms, methods of preparing the compounds of formula (IV) will be found in the following references:

DURGESHWARI P.; CHAUDHURY N. D.; J. Ind. Chem. Soc., 1962, 39, 735-6,

HEINZ P.; KREGLEWSKI A.; J. Prakt. Chem., 1963, 21(3-4), 186-197,

ZAUGG H. E.; DUNNIGAN D. A.; MICHAELS R. J.; SWETT L. R.; J. Org. Chem., 1961, 26, 644-51, KAGAN H. B.; HENG SUEN Y.; Bull. Soc. Chim. France, 1966(6), 1819-22, RATHKE M. W.; DEITCH J.; Tetrahedron Lett., 1971(31), 2953-6, BORRIES KUBEL; Liebigs Ann. Chem., 1980, 1392-1401, MARQUET J.; MORENO-MANAS M.; Chem. Lett., 1981, 173-6, IOFFE T.; POPOV E. M.; VATSURO K. V.; TULIKOVA E. K.; KABACHNIK M. I.; Tetrahedron, 1962, 18, 923-940, and SHEPHERD T. M.; Chem. Ind. (London), 1970, 17, 567.

In formula (III), W is a halogen atom, preferably chlorine or bromine.

In the same formula:

V can be a group

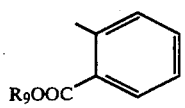

$R_9$ being a lower alkyl or benzyl radical, in which case the compounds of formula (III) are prepared by reacting a magnesium compound of p-bromotoluene with a compound of the formula

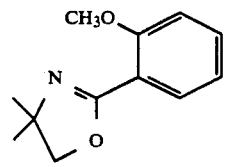

to give a compound of the formula which is then hydrolyzed to give the compound of the formula Procedures for the three steps described above will be found in the following reference:

MEYERS A. I.; MIHELICH E. D.; J. Am. Chem. Soc., 1975, 97, 7383.

The acid is then esterified with an alcohol of the formula $R_9OH$, $R_9$ being as defined above.

These derivatives are then brominated or chlorinated, for example with N-bromosuccinimide, N-chlorosuccinimide or bromine, in a solvent such as carbon tetrachloride, dibromoethane or dichloroethane, to give the compounds of formula (III) in which V is the group V can be the group

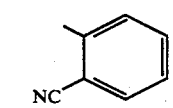

in which case the compound

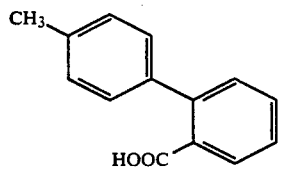

prepared above will be converted to the primary amide by reacting the acid chloride, obtained with thionyl chloride or phosphorus oxychloride, with aqueous ammonia, and this amide will be converted to the nitrile by reaction with phosphorus oxychloride in dimethylformamide or with thionyl chloride. Likewise the compound

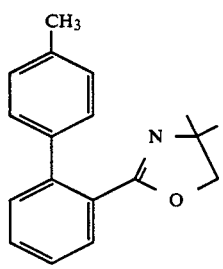

obtained above may be converted directly to the carbonitrile derivative by treatment in pyridine in the presence of POCl₃. The following nitrile derivative obtained:

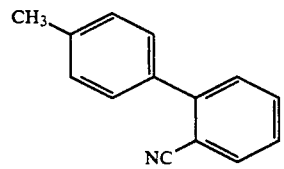

will then be brominated or chlorinated under the same conditions as the above ester to give the compounds of formula (III) in which V is the group

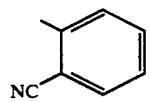

In formula (IV), R₁ and R₈ are as defined above and V is as defined in formula (III).

However, the compounds of formula (IV) in which V is a group

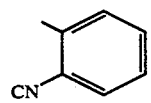

will react with one equivalent of sodium azide in a solvent such as dimethylformamide, in the presence of an ammonium salt such as ammonium chloride, or by heating in toluene or xylene with trimethyltin azide, to give the compounds of formula (IV) in which V is the group

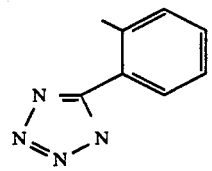

In formula (V), V is as defined in formula (III), but this condensation method will only be used when V possesses a group unaffected by hydrogenation.

Thus reaction of a compound of formula (VI):

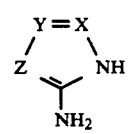

Formula (VI)

in which X, Y and Z are as defined above, with the compounds of formula (IV), in which R₁ and R₈ are as defined above and V is one of the following groups:

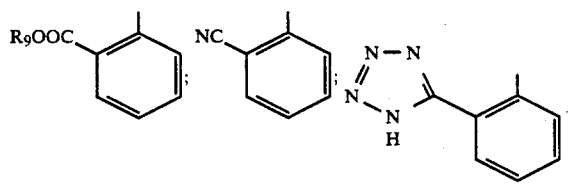

where R₉ is as defined above, will give the compounds of formulae (VIIa) and/or (VIIb):

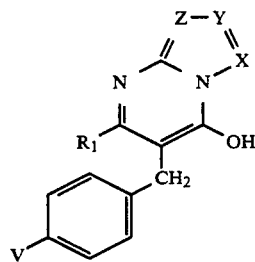
(VIIa)

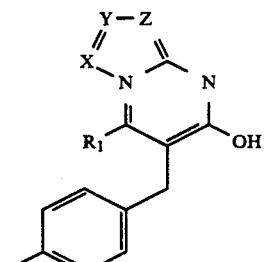
(VIIb)

and their tautomeric forms, in which R₁, X, Y, Z and V are as defined above, by condensation in an aprotic solvent such as trichlorobenzene or in an acid solvent such as acetic acid, at temperatures varying from 100° to 150° C.

In the case where V is the group

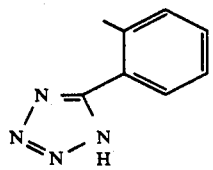

the reaction temperatures should not exceed 140° C. so as not to decompose the tetrazole.

The reaction of heteroaromatic amines with β-ketoesters is described well in the literature and, according to the operating conditions, the forms obtained are identified. Examples which may be cited are the studies by J. A. VAN ALLAN et al., J. Org. Chem., p. 779 to p. 801 (1959), and by L. A. WILLIAMS, J. Chem. Soc., p. 1829 (1960), and L. A. WILLIAMS, J. Chem. Soc., p. 3046 (1961).

Thus the compounds VIIa and VIIb will be identified for separate treatment.

For example, heating the derivatives of formulae (VIIa) and (VIIb) in POCl₃ will give the derivatives of formulae (VIIIa) and (VIIIb):

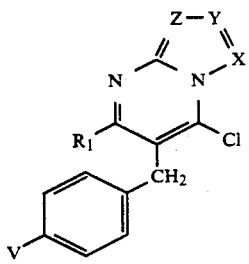

Formula (VIIIa)

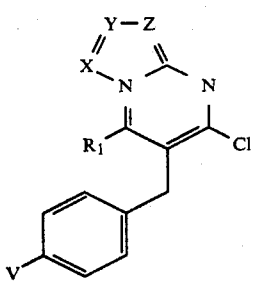

Formula (VIIIb)

in which R₁, X, Y, Z and V are as defined above.

The derivatives of formula (IX):

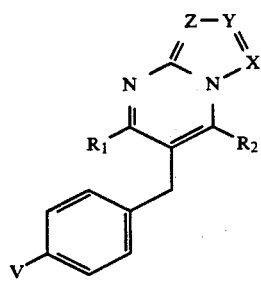

Formula (IX)

in which R₁, R₂, X, Y, Z and V are as defined above, will be obtained by heating the derivatives of formulae (VIIIa) and (VIIIb) in the presence of a nucleophile containing nitrogen, oxygen or sulfur, under reflux in an alcohol, in the presence or absence of a base such as Na₂CO₃, or in an autoclave at 100° C.

In the case of the triazolopyrimidines, these compounds (VIIa) and (VIIb) (case where only one of the radicals X, Y or Z is a group C-R₇, R₇ being as defined above) will be obtained by reacting the derivatives of formula (X):

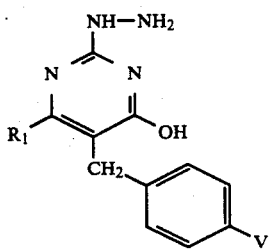

Formula (X)

in which R₁ and V are as defined above, with
  acids, acid chlorides or carboxylic acid esters,
  isocyanates or isothiocyanates,
  orthoesters,
  carbonyldiimidazole or
  urea, potassium xanthogenate, carbon disulfide or an analogous reagent, by heating without a solvent or in a solvent such as N-methylpyrrolidone, or an alcohol such as ethanol or methoxyethanol, in the presence or absence of a base such as triethylamine or pyridine.

According to the operating conditions, especially the temperature and pH of the reaction, s-triazolo[4,3-a]pyrimidine derivatives or their s-triazolo[1,5-a]pyrimidine rearrangement products will be obtained.

The compounds of formula (X) can be obtained by any one of the known methods of synthesizing 2-hydrazinopyrimidines (cf.: The Pyrimidines; The Chemistry of Heterocyclic Compounds; D. J. BROWN; Wiley Interscience 1970), especially by substitution of the derivatives of formula (XI):

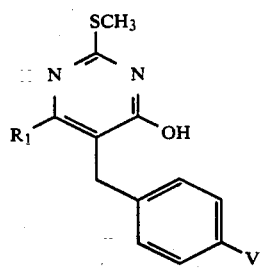

Formula (XI)

in which R₁ and V are as defined above, with hydrazine hydrate, for example.

The compounds of formula (XI) are obtained by condensing S-methylthiourea with the derivatives of formula (IV), for example, or by any one of the methods of synthesizing 2-thiomethylpyrimidines which are known in the literature (cf.: The Pyrimidines, op. cit.).

The compounds of formula (IX) in which V is the group

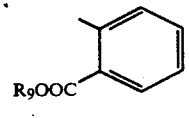

may be hydrolyzed in an acid or basic medium, or hydrogenated in the case where $R_9$ is a benzyl, to give the compounds of formula (I) in which $R_3$ is the group

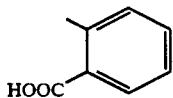

The compounds of formula (IX) in which V is a group

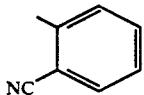

will react with one equivalent of sodium azide in a solvent such as dimethylformamide, in the presence of an ammonium salt such as ammonium chloride, or by heating in toluene or xylene with trimethyltin azide, followed by an acid treatment, for example with gaseous hydrochloric acid in tetrahydrofuran, to give the compounds of general formula (I) in which $R_3$ is a tetrazol-5-yl group.

The compounds of formula (IX) in which V is a group

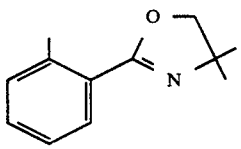

may be converted by hydrolysis to the group

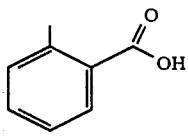

or by treatment with $POCl_3$ in the presence of pyridine to the group

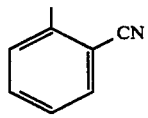

to give the compounds of formula (I) by the methods mentioned above.

It is possible to obtain addition salts of some of the compounds of formula (I), especially pharmaceutically acceptable addition salts. In particular, when the compounds of formula (I) contain an acid or tetrazole group, there may be mentioned the salts of sodium, potassium, calcium, an amine such as dicyclohexylamine or an amino acid such as lysine. When they contain an amine group, there may be mentioned the salts of an inorganic or organic acid, such as the hydrochloride, methanesulfonate, acetate, maleate, succinate, fumarate, sulfate, lactate or citrate.

The novel compounds according to the invention possess remarkable pharmacological properties as angiotensin II receptor antagonists and can be used in therapeutics for the treatment of cardiovascular diseases and in particular for the treatment of hypertension, cardiac insufficiency and diseases of the arterial wall.

Thus the invention covers the pharmaceutical compositions which contain as the active principle the drugs consisting of a pharmaceutically effective amount of at least one compound of formula (I) as defined above, as well as its pharmaceutically acceptable addition salts if appropriate.

These compositions can be administered by the buccal, rectal, parenteral, transdermal or ocular route.

These compositions can be solid or liquid and can take the pharmaceutical forms commonly used in human medicine, such as, for example, simple or coated tablets, gelatin capsules, granules, suppositories, injectable preparations, transdermal systems and eye lotions. They are prepared by the customary methods. In said compositions, the active principle, consisting of a pharmaceutically effective amount of at least one compound of formula (I) as defined above, or one of its pharmaceutically acceptable addition salts, can be incorporated with excipients normally employed in these pharmaceutical compositions, such as talc, gum arabic, lactose, starch, magnesium stearate, polyvidone, cellulose derivatives, cocoa butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavorings and colors.

The invention also covers a pharmaceutical composition with antagonistic activity towards angiotensin II receptors, which makes it possible especially to favorably treat cardiovascular diseases, in particular hypertension, cardiac insufficiency and diseases of the arterial wall, said composition comprising a pharmaceutically effective amount of at least one compound of formula (I) mentioned above, or one of its pharmaceutically acceptable addition salts, which may be incorporated in a pharmaceutically acceptable excipient, vehicle or carrier.

The dosage varies especially according to the route of administration, the complaint treated and the subject in question.

For example, for an adult with an average weight of 60 to 70 kg, it can vary between 1 and 400 mg of active principle, administered orally in one or more daily doses, or from 0.01 to 50 mg, administered parenterally in one or more daily doses.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. This pharmaceutical composition can be formulated as gelatin capsules or tablets containing from 1 to 400 mg of active principle, or as injectable preparations containing from 0.01 to 50 mg of active principle.

The invention also covers a method of therapeutic treatment for mammals, which comprises administering to this mammal a therapeutically effective amount of at least one compound of formula (I) as defined above, or one of its pharmaceutically acceptable addition salts.

In animal therapeutics, the daily dose which can be used should normally be between 1 and 100 mg per Further characteristics and advantages of the invention will be understood more clearly from the following description of some Preparatory Examples, which in no way imply a limitation but are given by way of illustration.

EXAMPLE 1

Ethyl 3-oxohexanoate

Formula (II): $R_1$=n-propyl, $R_8$=ethyl 176 g of 2,2-dimethyl-4,6-dioxo-1,3-dioxane (Meldrum's acid) are dissolved in 550 ml of methylene chloride and 188 ml of pyridine. The mixture is cooled to 5° C. with a bath of water and ice and 133 ml of butyryl chloride are added dropwise. When the addition is complete, the mixture is stirred for three hours at room temperature. The solution is washed with a dilute solution of hydrochloric acid, dried over magnesium sulfate and evaporated under vacuum to give an oil. This oil is dissolved in 700 ml of ethanol and the mixture is refluxed for six hours. The ethanol is evaporated off under vacuum and the residue obtained is distilled to give 145.4 g of ethyl 3-oxohexanoate in the form of an oil.

Boiling point (20 mm of mercury): 98°–100° C.

The compound of Example 2 was prepared by the procedure of Example 1.

EXAMPLE 2

Ethyl 3-oxoheptanoate

Formula (II): $R_1$=n-butyl, $R_8$=ethyl

Boiling point (20 mm of mercury): 115°–120° C.

EXAMPLE 3

4'-Bromomethyl-2-cyanobiphenyl

Formula (III): W=Br, V=CN

Preparation of 2-cyano-4'-methylbiphenyl 563.8 g of (4'-methylbiphenyl-2-yl)carboxylic acid, prepared according to MEYERS A. I., MIHELICH E. D.; J. Am. Chem. Soc., 1975, 97(25), 7383, are added in small portions to 800 ml of thionyl chloride. The mixture is refluxed for two hours. The thionyl chloride is concentrated under vacuum and the residue is poured into a 28% solution of ammonium hydroxide cooled beforehand with a bath of water and ice. The mixture is stirred for 30 minutes and the crystals obtained are filtered off, washed with water followed by ether and then dried to give 554.8 g of (4'-methylbiphenyl-2-yl)-carboxamide in the form of crystals melting at 128°–132° C. These crystals are taken up in 1300 ml of thionyl chloride and the mixture is refluxed for 3 hours and then concentrated under vacuum to give an orange oil. This is taken up in two liters of chloroform and washed with water and the organic phase is then dried and concentrated to give 509.8 g of an oil, which crystallizes from pentane to give 467.3 g of 2-cyano-4'-methylbiphenyl.

Melting point: 46°–48° C.

The 467.3 g of 2-cyano-4'-methylbiphenyl prepared above are dissolved in 4.7 l of 1,2-dichloroethane in the presence of 467.3 g of N-bromosuccinimide and 9.3 g of benzoyl peroxide. The mixture is heated very gradually so as to have good control over the exothermic effect. It is subsequently refluxed for 4 h, cooled to 50° C. and then washed 3 times with hot water and dried and the organic phase is concentrated to give cream-colored crystals.

Recrystallization from isopropanol gives 451 g of white crystals of 4'-bromomethyl-2-cyanobiphenyl.

Melting point: 128° C.

EXAMPLE 4

Ethyl 2-[(2'-cyanobiphenyl-4-yl)methyl]-3-oxohexanoate

Formula (IV): $R_1$=n-propyl, $R_8$=ethyl,

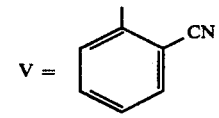

23 g of the ethyl 3-oxohexanoate prepared in Example 1 are dissolved in 120 ml of tetrahydrofuran. 30.3 g of the 4'-bromomethyl-2-cyanobiphenyl prepared in Example 3 and 4.7 g of lithium chloride are added and the mixture is stirred at room temperature. 39 ml of diisopropylethylamine are then added dropwise, causing a slight exothermic effect. The mixture is subsequently stirred for three hours at room temperature and then for ten hours under reflux. The solvents are evaporated off under vacuum and the residue is taken up in water and then extracted with chloroform. The organic phase is decanted and then washed with a dilute solution of hydrochloric acid, dried over magnesium sulfate and evaporated under vacuum to give 38 g of an orange oil.

Purification by chromatography on silica gel (eluent: $CHCl_3$) gives 32.3 g of ethyl 2-[(2'-cyanobiphenyl-4-yl)methyl]-3-oxohexanoate.

The compound of Example 5 is obtained by the procedure of Example 4, except that the ethyl 3-oxoheptanoate prepared in Example 2 is used.

EXAMPLE 5

Ethyl 2-[(2'-cyanobiphenyl 4-yl)methyl]-3-oxoheptanoate

Formula (IV): $R_1$=n-butyl, $R_8$=ethyl,

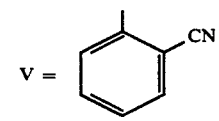

Oil used as such for the next step.

EXAMPLE 6

Ethyl 2-[[2'-(1H-tetrazol-5-yl)biphenyl-4-yl]methyl]-3-oxoheptanoate

Formula (IV): $R_1$=n-propyl, $R_8$=ethyl,

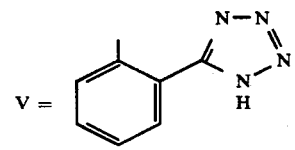

A mixture of 69.9 g of the ethyl 2-[(2'-cyanobiphenyl-4-yl)methyl]-3-oxohexanoate prepared according to Example 4, 700 ml of anhydrous toluene and 47.5 g of trimethyltin azide, prepared from sodium azide and trimethyltin chloride, is refluxed for 24 h. A further 47.5 g of trimethyltin azide are added and reflux is continued for 16 h. The mixture is concentrated to 50%. The orange solution obtained is purified by chromatography twice in succession (eluent: chloroform 90%/methanol 10%, then chloroform 95%/methanol 5%) to give 58 g of an orange oil, which crystallizes after one month.

Melting point: 65° C.

EXAMPLE 7

Method A 6-(2'-Cyanobiphenyl-4-yl)methyl]-7-hydroxy-5-propyl-1,2,4-triazolo[1,5-a]pyrimidine Formula (VIIa): R=n-propyl, X=N, V = 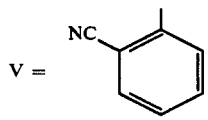

1.7 g of 3-amino-1,2,4-triazole, 7 g of the β-ketoester prepared in Example 4 and 30 ml of acetic acid are refluxed for 6 h. The acetic acid is evaporated off. The oil obtained is purified by chromatography on silica gel (eluent: CHCl₃ 90%/MeOH 10%) to give 5.2 g of the starting β-ketoester and 1.2 g of 6-[(2'-cyanobiphenyl-4-yl)methyl]-7-hydroxy-5-propyl-1,2,4-triazolo[1,5-a]pyrimidine.

Melting point: 200°-205° C.

$^1$H NMR (200 MHz; DMSO-$d_6$): 2.65 (t, 2H, propyl CH$_2$); 8.2 (s, 1H, H$_2$)

UV (10 μg/ml, MeOH): $\lambda_a$=209.1 nm $\lambda_b$=257.7 nm $\lambda_c$=286.8 nm

EXAMPLE 8

Method B

6-[(2'-Cyanobiphenyl-4-yl)methyl]-5-hydroxy-7-propyl 1,2,4-triazolo[1,5-a]pyrimidine Formula (VIIb): R$_1$=n-propyl, X=N, Y=CH, Z=N, V=

V = 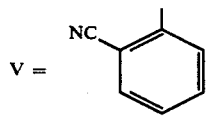

7.1 g of the β-ketoester prepared in Example 4, 1.7 g of 3-amino-1,2,4-triazole and 70 ml of 1,2,4-trichlorobenzene are refluxed for 7 h. The mixture is concentrated under vacuum. The thick oil obtained is chromatographed on silica gel (eluent: CHCl₃ 95%/MeOH 5%) to give 0.8 g of the isomer obtained in Example 7 (melting point: 200° C.) and 2.2 g of 6-[(2'-cyanobiphenyl-4-yl)methyl]-5-hydroxy-7-propyl-1,2,4-triazolo[1,5-a]pyrimidine.

Melting point: 212° C.

$^1$H NMR (DMSO-$d_6$): 2.98 (t, 2H, propyl CH$_2$); 8.1 (s, 1H, H$_2$)

UV (10 μg/ml, MeOH): $\lambda_a$=207.5 nm, $\lambda_b$=258.2 nm

EXAMPLE 9

Method C

6-[(2'-Cyanobiphenyl-4-yl)methyl]-5-hydroxy-7-propyl-1,2,4 triazolo[4,3-a]pyrimidine Formula (VIIa): R$_1$=n-propyl, X=CH, V = 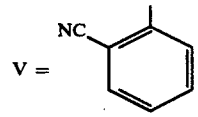

a) 5-[(2'-Cyanobiphenyl-4 yl)methyl]-4-hydroxy-6-propyl-2-thiolpyrimidine 11 g of thiourea are added with a spatula to a solution of sodium methanolate prepared from 4.6 g of sodium and 150 ml of methanol. 34.9 g of the β-ketoester prepared in Example 4, dissolved in 50 ml of methanol, are then added dropwise. The mixture is left to stand overnight and then refluxed for 7 h. It is concentrated under vacuum, taken up with 500 ml of water and then acidified with concentrated HCl to bring the pH to 1. The gummy precipitate is isolated and taken up in methanol to give 17.3 g of white crystals of 5-[(2'-cyanobiphenyl-4-yl)methyl]-4-hydroxy-6-propyl-2-thiolpyrimidine.

Melting point: 196° C.

b) 5 [(2'-Cyanobiphenyl-4 yl)methyl]-4-hydroxy-2-methylmercapto-6-propyl-pyrimidine Formula (XI): R$_1$=n-propyl, V = 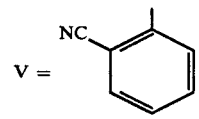

The 17.3 g of compound obtained above are added in portions to a mixture of 340 ml of methanol and 2.9 g of KOH. After a clear solution has formed, it is cooled and 3.4 ml of ICH₃ are then added dropwise.

The mixture is left to react for 2 h at room temperature.

The precipitate is filtered off to give 17.2 g of 5-[(2'-cyanobiphenyl-4-yl)methyl]-4-hydroxy-2-methylmercapto-6-propylpyrimidine.

Melting point: 220° C.

c) 5-[(2'-Cyanobiphenyl-4-yl)methyl]-2-hydrazino-4 hydroxy-6-propylpyrimidine

Formula (X): R$_1$=n-propyl,

V = 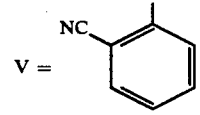

12.4 g of the 5-[(2'-cyanobiphenyl-4-yl)-methyl]-4-hydroxy-2-methylmercapto-6-propylpyrimidine prepared above are dissolved in 370 ml of 2-methoxyethanol. 33 ml of hydrazine hydrate are added and the mixture is then refluxed for 3 h. It is concentrated under vacuum, taken up in acetonitrile and triturated. The solid obtained is filtered off and washed with ether and isopropyl ether to give 9.9 g of 5-[(2'-cyanobiphenyl-4-yl)methyl]-2-hydrazino-4-hydroxy-6-propylpyrimidine.

Melting point: 191° C.

d) 6-[(2'-Cyanobiphenyl-4-yl)methyl]-5-hydroxy-7-propyl-1,2,4 triazolo[4,3-a]pyrimidine Formula (VIIa): $R_1$ = n-propyl, X = CH,

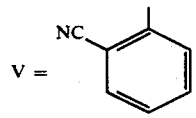

10 g of 5-[(2'-cyanobiphenyl-4-yl)methyl]-2-hydrazino-4-hydroxy-6-propylpyrimidine prepared as above are placed in 100 ml of formic acid. The mixture is refluxed for 4 h. It is concentrated under reduced pressure and the thick oil obtained is taken up in water and triturated until it crystallizes.

The compound is purified by chromatography on silica gel (eluent: $CHCl_3$ 95%/methanol 5%).

This gives 8.3 g of 6-[(2'-cyanobiphenyl-4-yl)methyl]-5-hydroxy-7-propyl-1,2,4-triazolo[4,3-a]pyrimidine.

Melting point: 217° C.

$^1$H NMR (DMSO-$d_6$): 2.6 (t, 2H, propyl $CH_2$); 9 (s, 1H, $H_3$)

UV (10 µg/ml, MeOH): $\lambda_a$ = 210.2 nm, $\lambda_b$ = 257.5 nm, $\lambda_c$ = 303.4 nm

EXAMPLE 10

6-[(2'-Cyanobiphenyl-4-yl)methyl]-7-hydroxy-5-propyl-1,2,4-triazolo[4,3-a]-pyrimidine Formula (VIIb): $R_1$ = n-propyl, X = CH, Y = N, Z = N, V =

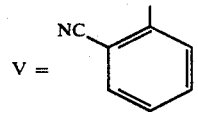

Following the procedure of Example 9, step d), 1.1 g of 6-[(2'-cyanobiphenyl-4-yl)methyl]-7-hydroxy-5-propyl-1,2,4-triazolo[4,3-a]pyrimidine are obtained at the same time as the compound described above.

Melting point: 204°-206° C.

$^1$H NMR (DMSO-$d_6$): 2.9 (t, 2H, propyl $CH_2$); 9 (s, 1H, $H_3$)

UV (10 µg/ml, MeOH): $\lambda_a$ = 211.5 nm, $\lambda_b$ = 260 nm

The compounds of Examples 9 and 10 can also be obtained by reacting compound 9 c) with triethyl orthoformate under reflux for 5 h. In this case the proportion of the compound of Example 10 is found to be slightly improved.

EXAMPLE 11

Method D

6-[(2'-Cyanobiphenyl-4 yl)methyl]-7-hydroxy 5-propyl 1,2,4-triazolo[1,5-a]-pyrimidine Formula (VIIa): $R_1$ = n-propyl, X = N, Y = CH, Z = N, V =

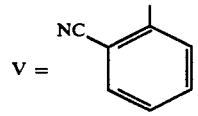

500 mg of the 6-[(2'-cyanobiphenyl-4-yl)-methyl]-5-hydroxy-7-propyl-1,2,4-triazolo[4,3-a]pyrimidine prepared in Example 9 d) are heated in a metal bath at 225° C. for 2 h 30 min. It is left to cool and taken up with methanol and then with isopropyl acetate to give 300 mg of cream-colored crystals identical to the compound of Example 7.

Melting point: 200° C. The compounds of Examples 12 and 13 were prepared by method A described above for Example 7, except that appropriate 3-aminopyrazoles were used.

EXAMPLE 12

6-[(2'-Cyanobiphenyl-4-yl)methyl]-7-hydroxy-5-propylpyrazolo[1,5-a]pyrimidine

Formula (VIIa): $R_1$ = n-propyl, X = N, Y = CH, Z = CH, V =

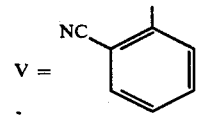

Melting point: 251° C.

$^1$H NMR (DMSO-$d_6$): 2.65 (t, 2H, propyl $CH_2$); 6.1 (d, 1H, $H_3$); 7.85 (d, 1H, $H_2$); J($H_2$-$H_3$) = 2 Hz

EXAMPLE 13

6-[(2'-Cyanobiphenyl-4 yl)methyl]-7-hydroxy-2-methyl-5-n-propylpyrazolo[1,5a]-pyrimidine Formula (VIIa): $R_1$ = n-propyl, X = N, Y = C—$CH_3$, Z = CH, V =

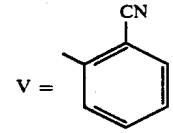

Melting point: 210° C.

$^1$H NMR (DMSO-$d_6$): 2.3 (s, 3H, $CH_3$); 2.6 (t, 2H, propyl $CH_2$); 5.9 (s, 1H, $H_3$)

6-[(2'cyanobiphenyl-4-yl)methyl]-7-hydroxy-2-methyl-5-propyl-1,2,4-triazolo-[1,5-a]pyrimidine hydrochloride Formula (VIIa): $R_1$ = n-propyl, X = N, Y = C-$CH_3$, Z = N, V =

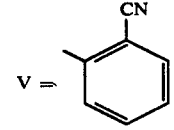

A suspension of 10 g of compound 9 c) in 100 ml of phenyl acetate is refluxed for 4 h. It is concentrated under reduced pressure, taken up in water and extracted with chloroform and the extract is dried and evaporated to give 9.8 g of white crystals melting at 205° C. These crystals are taken up in 50 ml of acetonitrile and 40 ml of a 10% solution of hydrochloric acid in ether to give 7.5 g of 6-[(2'-cyanobiphenyl-4-yl)methyl]-5-hydroxy-2-methyl-7-propyl-1,2,4-triazolo-[4,3-a]pyrimidine hydrochloride.

Melting point: 190° C.

$^1$H NMR (DMSO-d$_6$): 2.65 (t, 2H, propyl CH$_2$)

UV (MeOH): $\lambda_a$=213.7 nm, $\lambda_b$=257.7 nm, $\lambda_c$=285 nm

EXAMPLE 15

6-[(2'-Cyanobiphenyl-4-yl)methyl]-5-hydroxy-7-propyl-3-thiol-1,2,4-triazolo-[4,3-a]pyrimidine Formula (VIIa): R$_1$=n-propyl, X=C—SH, Y=N, Z=N, V=

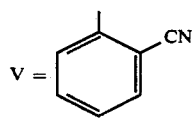

5.3 ml of carbon disulfide are added to a suspension of 10 g of the compound prepared in Example 9 c) in 300 ml of butanol. The mixture is refluxed for 2h. A further 5.3 ml of CS$_2$ are added and the mixture is then refluxed for 5 h. It is concentrated under vacuum, taken up with water and extracted 3 times with chloroform. The solvent is evaporated off to give 10.8 g of amorphous crystals, which are purified by chromatography on silica gel (eluent: CHCl$_3$ 90%/MeOH 10%).

A first compound, weighing 1.9 g, is isolated and identified as 6-[(2'-cyanobiphenyl-4-yl)methyl]-7-hydroxy-5-propyl-3-thiol-1,2,4-triazolo[4,3-a]pyrimidine, which is the product of Example 15 bis.

Melting point: 240° C.

$^1$H NMR (DMSO-d$_6$): 3.5 (t, 2H, propyl CH$_2$)

A second compound, weighing 1 g, is the expected product: 6-[(2'-cyanobiphenyl-4-yl)methyl]-5-hydroxy-7-propyl-3-thiol-1,2,4-triazolo[4,3-a]pyrimidine.

Melting point: 180° C.

$^1$H NMR (DMSO-d$_6$): 2.5 (m, propyl CH$_2$+DMSO-d$_6$)

The third product, weighing 3.2 g, is the starting hydrazino compound 9 c).

EXAMPLE 16

6-[(2'-Cyanobiphenyl-4 yl)methyl]-3,5-dihydroxy-7-propyl-1,2,4-triazolo[4,3-a]-pyrimidine Formula (VIIa): R$_1$=n-propyl, X=C—OH, Y=N, Z=N, V=

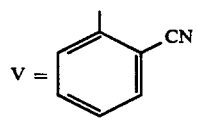

4.6 g of carbonyldiimidazole are added to a mixture of 10 g of the compound prepared in Example 9 c) and 500 ml of THF, heated to 50° C. The whole is refluxed for 7 h. It is concentrated under vacuum, taken up with water and extracted three times with chloroform. Evaporation of the solvent gives 12.4 g of amorphous crystals, which are purified by chromatography on silica gel (eluent: CHCl$_3$ 95%/MeOH 5%).

A first compound, weighing 3.1 g, is isolated and identified as 6-[(2'-cyanobiphenyl-4-yl)methyl]-3,7-dihydroxy-5-propyl-1,2,4-triazolo[4,3-a]pyrimidine, which is the product of Example 16 bis.

Melting point: 228° C.

$^1$H NMR (DMSO-d$_6$): 3 (t, 2H, propyl CH$_2$)

The second compound, weighing 3.8 g, is the expected product: 6-[(2'-cyanobiphenyl-4-yl)methyl]-3,5-dihydroxy-7-propyl-1,2,4-triazolo[4,3-a]pyrimidine.

Melting point: 210° C.

$^1$H NMR (DMSO-d$_6$) 2.4 (t, 2H, propyl CH$_2$)

EXAMPLE 17

7 Chloro 6-[(2'-cyanobiphenyl-4-yl)methyl]-5-propyl-pyrazolo[1,5-a]pyrimidine

Formula (VIIIa): R$_1$=n-propyl, X=N, Y=CH, Z=CH, V=

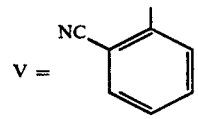

27 g of the 6-[(2'-cyanobiphenyl-4-yl)methyl]-7-hydroxy-5-propylpyrazolo[1,5-a]pyrimidine prepared in Example 12 are added in portions to 540 ml of POCl$_3$. The mixture is refluxed for 3 h. It is concentrated under vacuum. The oil obtained is taken up with methylene chloride and washed twice with a solution of water and ice. The organic phase is decanted, dried and concentrated. The yellow oil is taken up in ether to give 25.6 g of crystals of 7-chloro-6-[(2'-cyanobiphenyl-4-yl)methyl]-5-propylpyrazolo[1,5-a]pyrimidine.

Melting point: 137° C.

$^1$H NMR (CDCl$_3$): 2.8 (t, 2H, propyl CH$_2$); 6.7 (d, 1H, H$_3$); 8.2 (d, 1H, H$_2$); J(H$_2$–H$_3$)=2.2 Hz

EXAMPLE 18

6-[(2'-Cyanobiphenyl-4-yl)methyl]-7-[2-(morpholin-4-yl)ethylamino]-5-propylpyrazolo[1,5-a]pyrimidine Formula (IX): R$_1$=n-propyl, X=N, Y=CH, Z=CH, V=

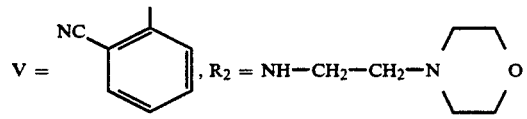

A mixture of 5 g of the chlorinated derivative prepared in Example 17, 1.8 g of 4-(2-aminoethyl)morpholine, 1.5 g of Na$_2$CO$_3$ and 100 ml of ethanol is refluxed for 7 h. A further 1.8 g of 4-(2-aminoethyl)morpholine are added and the mixture is refluxed for 8 h. It is concentrated under vacuum and taken up with a mixture of water and methylene chloride. The aqueous phase is decanted and extracted with methylene chloride. The organic phases are combined and dried. Evaporation of the solvent gives 5.9 g of a brown oil which is sufficiently pure for the next step.

$^1$H NMR (CDCl$_3$): 2.5 (t, 2H, propyl CH$_2$); 6.4 (d, 1H, H$_3$); 7.9 (d, 1H, H$_2$); J(H$_2$–H$_3$)=2.4 Hz The compounds of Examples 19 and 20 were obtained according to Example 18, except that the appropriate amines were used.

EXAMPLE 19

6-[(2'-Cyanobiphenyl-4-yl)methyl]-7-(N-morpholino)-5-propylpyrazolo[1,5 a]pyrimidine Formula (IX): $R_1$=n-propyl, $R_2$=N-morpholino, X=N, Y=CH, Z=CH, V=

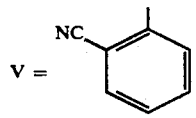

Melting point: 140° C.

$^1$H NMR (DMSO-d$_6$): 2.6 (t, 2H, propyl CH$_2$); 6.6 (d, 1H, H$_3$); 8.1 (d, 1H, H$_2$); J(H$_2$-H$_3$)=2.4 Hz

EXAMPLE 20

6-[(2'-Cyanobiphenyl-4-yl)methyl]-5-propyl-7-[2-(pyrrolidin-1-yl)ethylamino]pyrazolo-[1,5-a]pyrimidine Formula (IX): $R_1$=n-propyl, X=N, Y=CH, Z=CH,

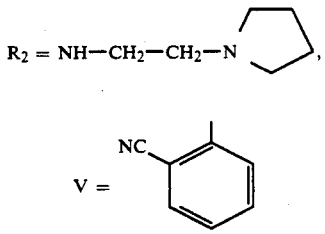

Oil purified by chromatography on silica gel (eluent: CHCl$_3$ 90%/methanol 10%).

$^1$H NMR (CDCl$_3$): 2.6 (m, 4H, propyl CH$_2$+pyrrolidine CH$_2$); 6.4 (d, 1H, H$_3$); 7.9 (d, 1H, H$_2$); J(H$_2$-H$_3$)=2.1 Hz The compounds of Examples 21 and 22 were obtained by the same procedure, except that the reaction was carried out in an autoclave at 100° C. for 48 h.

EXAMPLE 21

6-[(2'-Cyanobiphenyl-4-yl)methyl]-7-N,N-diethylamino-5-propylpyrazolo[1,5-a]pyrimidine Formula (IX): $R_1$=n-propyl, X=N, Y=CH, Z=CH,

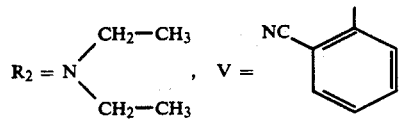

Oil purified by chromatography on silica gel (eluent: CH$_2$Cl$_2$ 95%/ethyl acetate 5%).

$^1$H NMR (DMSO-d$_6$): 2.6 (t, 2H, propyl CH$_2$); 6.6 (d, 1H, H$_3$); 8.1 (d, 1H, H$_2$); J(H$_2$-H$_3$)=2.1 Hz

EXAMPLE 22

7-Amino-6-[(2'-cyanobiphenyl-4-yl)methyl]-5-propylpyrazolo[1,5-a]pyrimidine

Formula (IX): $R_1$=n-propyl, $R_2$=NH$_2$, X=N, Y=CH, Z=CH,

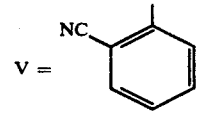

Oil purified by chromatography on silica gel (eluent: CH$_2$Cl$_2$ 95%/acetone 5%). Crystallizes slowly.

Melting point: 158° C.

$^1$H NMR (CDCl$_3$): 2.7 (t, 2H, propyl CH$_2$); 6.4 (d, 1H, H$_3$); 7.9 (d, 1H, H$_2$); J(H$_2$-H$_3$)=2 Hz

EXAMPLE 23

7-Hydroxy-5-propyl-6 [(2'-(1H-tetrazol-5-yl)biphenyl-4-yl)methyl]-pyrazolo[1,5-a]-pyrimidine Formula (I): $R_1$=n-propyl, $R_2$=OH, $R_3$=1H-tetrazol-5-yl, X=N, Y=CH, Z=CH A mixture of 0.8 g of 3-aminopyrazole, 3.9 g of the β-ketoester of Example 6 and 25 ml of acetic acid is refluxed for 6 h. 0.4 g of aminopyrazole is added and the mixture is refluxed for a period of 6 h. It is concentrated under vacuum. The oil obtained is taken up in water to give 3.8 g of a solid, which is purified a first time by chromatography on silica gel (eluent: chloroform 80%/methanol 20% to remove the less polar products, then chloroform 70%/methanol 30% to elute the pyrazolopyrimidine compound). The resulting solid is treated with a normal solution of sodium hydroxide. The insoluble materials are removed and the clear solution is acidified to pH 4 by bubbling SO$_2$ to give a white precipitate. The compound is crystallized from ethanol to give 0.6 g of 7-hydroxy-5-propyl-6-[(2'-(1H-tetrazol-5-yl)biphenyl-4-yl)methyl]pyrazolo[1,5-a]pyrimidine.

Empirical formula: C$_{23}$H$_{21}$N$_7$O.2H$_2$O

Melting point: ≧320° C. with decomposition.

$^1$H NMR (DMSO-d$_6$): 2.5 (m, 2H, propyl CH$_2$+DMSO-d$_6$); 6 (d, 1H, H$_3$); 7.8 (d, 1H, H$_2$); J(H$_2$-H$_3$)=1.9 Hz

EXAMPLE 24

7-Hydroxy-5-propyl 6-[(2'-(1H-tetrazol-5-yl)biphenyl-4-yl)methyl]-1,2,4-triazolo-[1,5-a]pyrimidine Formula (I): $R_1$=n-propyl, $R_2$=OH, $R_3$=1H-tetrazol-5-yl, X=N, Y=CH, Z=N A mixture of 7.8 of the β-ketoester of Example 6, 1.7 g of 3-amino-1,2,4-triazole and 70 ml of 1,2,4-trichlorobenzene is heated at 120° C. for 7 h. The precipitate obtained is purified a first time by chromatography on silica gel (eluent: CH$_2$Cl$_2$ 80%/methanol 20%). The compound obtained is dissolved in a 1 N solution of NaOH, the insoluble material is filtered off and the clear solution is acidified by bubbling SO$_2$ to give 2.4 g of a white precipitate of 7-hydroxy-5-propyl-6-[(2'-(1H-tetrazol-5-yl)biphenyl-4-yl)methyl]-1,2,4-triazolo[1,5-a]pyrimidine.

Empirical formula: C$_{22}$H$_{20}$N$_8$O.0.5H$_2$O

Melting point: 260°-265° C. with decomposition.

$^1$H NMR (DMSO-d$_6$): 2.6 (t, 2H, propyl CH$_2$); 8.2 (s, 1H, H$_2$)
UV (MeOH): λ$_a$=210 nm, λ$_b$250 nm

EXAMPLE 25

7-[(N-Morpholinoethyl)amino]-5-propyl 6-[(2'-(1H-tetrazol-5-yl)biphenyl-4-yl)-methyl]-pyrazolo[1,5-a]pyrimidine Formula (I): R$_1$=n-propyl, R$_3$=1H-tetrazol-5-yl, X=N, Y=CH, Z=CH,

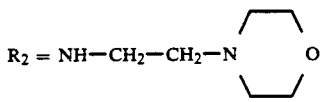

A mixture of 5.9 g of the 6-[(2'-cyanobiphenyl-4-yl)methyl]-7-[2-(morpholin-4-yl)ethylamino]-5-propyl-pyrazolo[1,5-a]pyrimidine prepared in Example 18, 3.1 g of trimethyltin azide and 120 ml of xylene is brought to the reflux point. After 15 h, a further 3.1 g of trimethyltin azide are added and the reflux reaction is continued for 20 h.

The thick oil is decanted from the xylene and taken up in THF. Acidification with gaseous hydrochloric acid gives a gummy precipitate, which is taken up with acetonitrile to give 4.7 g of a solid.

The base is freed by treatment with a solution of triethylamine/ethyl acetate. The compound is purified a first time by chromatography on silica gel (eluent: chloroform 80%/methanol 20%).

Recrystallization from ethanol gives 2.5 g of white crystals of 7-[(N-morpholinoethyl)amino]-5-propyl-6-[(2'-(1H-tetrazol-5-yl)biphenyl-4-yl)methyl]-pyrazolo[1,5-a]pyrimidine.

Empirical formula: C$_{29}$H$_{33}$N$_9$O.0.1H$_2$O
Melting point: 210° C.
$^1$H NMR (DMSO-d$_6$): 2.6 (t, 2H, propyl CH$_2$); 6.3 (d, 1H, H$_3$); 8 (d, 1H, H$_2$); J(H$_2$–H$_3$)=2.2 Hz The following compounds of Examples 26 to 30 were prepared by any one of the methods described in Examples 23, 24 or 25.

EXAMPLE 26

7-Hydroxy 2-methyl 5-propyl-6 [(2'-(1H-tetrazol-5 yl)biphenyl-4-yl)methyl]pyrazolo[1,5-a]pyrimidine hydrochloride Formula (I): R$_1$=n-propyl, R$_2$=OH, R$_3$=1H-tetrazol-5-yl, X=N, Y=C-CH$_3$, Z=CH
Empirical formula: C$_{24}$H$_{23}$N$_7$O.HCl.0.2H$_2$O
Melting point: 230°–232° C. with decomposition.
$^1$H NMR (DMSO-d$_6$): 2.6 (t, 2H, propyl CH$_2$); 6 (s, 1H, H$_3$)

EXAMPLE 27

7-Chloro-5-propyl6-[(2'-(1H-tetrazol-5-yl)biphenyl-4-yl)methyl]pyrazolo[1,5-a]-pyrimidine Formula (I): R$_1$=n-propyl, R$_2$=Cl, R$_3$=1H-tetrazol-5-yl, X=N, Y=CH, Z=CH
Empirical formula: C$_{23}$H$_{20}$ClN$_7$
Melting point: 234° C.
$^1$H NMR (DMSO-d$_6$): 2.7 (t, 2H, propyl CH$_2$); 6.8 (d, 1H, H$_3$); 8.3 (d, 1H, H$_2$); J(H$_2$–H$_3$)=2.3 Hz

EXAMPLE 28

7-(N-Morpholino)-5-propyl-6-[(2'-(1H-tetrazol-5-yl)biphenyl-4-yl)methyl]pyrazolo[1,5-a]pyrimidine hydrochloride Formula (I): R$_1$=n-propyl, R$_3$=1H-tetrazol-5-yl, X=N, Y=CH, Z=CH,

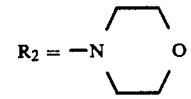

Empirical formula: C$_{27}$H$_{28}$N$_8$O.HCl
Melting point: 210°–212° C.
$^1$H NMR (DMSO-d$_6$): 2.8 (t, 2H, propyl CH$_2$); 6.6 (d, 1H, H$_3$); 8.2 (d, 1H, H$_2$); J(H$_2$–H$_3$)=2.2 Hz

EXAMPLE 29

7-Hydroxy-2-methyl-5-propyl-6-[(2'-(1H-tetrazol-5-yl)biphenyl-4-yl)methyl]-1,2,4-triazolo[1,5-a]pyrimidine hemisulfate Formula (I): R$_1$=n-propyl, R$_2$=OH, R$_3$=1H-tetrazol-5-yl, X=N, Y=C-CH$_3$, Z=N
Empirical formula: C$_{23}$H$_{22}$N$_8$O.0.5H$_2$SO$_4$
Melting point: 236°–238° C.
$^1$H NMR (DMSO-d$_6$): 2.6 (t, 2H, propyl CH$_2$)
UV (MeOH): λ$_a$212.1 nm, λ$_b$=250 nm

EXAMPLE 30

5-Propyl-7-[(N-pyrrolidinoethyl)amino]-6-[(2'-(1H-tetrazol-5-yl)biphenyl-4-yl)-methyl]pyrazolo[1,5-a]pyrimidine Formula (I): R$_1$=n-propyl, R$_3$=1H-tetrazol-5-yl, X=N, Y=CH, Z=CH,

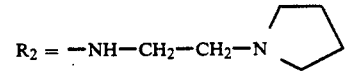

Empirical formula: C$_{29}$H$_{33}$N$_9$
Melting point: 200°–201° C.
$^1$H NMR (DMSO-d$_6$): 2.6 (t, 2H, propyl CH$_2$); 6.4 (d, 1H, H$_3$); 8 (d, 1H, H$_2$); J(H$_2$–H$_3$)=2 Hz

EXAMPLE 31

7-Amino-6-[(2'-(1H-tetrazol-5-yl)biphenyl-4-yl)methyl]-5-propylpyrazolo[1,5-a]-pyrimidine Formula (I): R$_1$=n-propyl, R$_2$=NH$_2$, R$_3$=1H-tetrazol-5-yl, X=N, Y=CH, Z=CH
Empirical formula: C$_{23}$H$_{22}$N$_8$
Melting point: 255° C.
$^1$H NMR (DMSO-d$_6$): 2.5 (m, 2H, propyl CH$_2$+DMSO-d$_6$); 6.3 (d, 1H, H$_3$); 8 (d, 1H, H$_2$); J(H$_2$–H$_3$)=2 Hz

EXAMPLE 32

6-[(2'-(1H-tetrazol-5-yl)biphenyl-4-yl)methyl]-5-hydroxy-7-propyl-1,2,4-triazolo[4,3-a]pyrimidine Formula (I): R$_1$=n-propyl, R$_2$=OH, R$_3$=1H-tetrazol-5-yl, X=CH, Y=N, Z=N
Empirical formula: C$_{22}$H$_{20}$N$_8$o
Melting point: 251° C.

$^1$H NMR (DMSO-d$_6$): 2.55 (t, 2H, propyl CH$_2$); 9 (s, 1H, H$_3$)

PHARMACOLOGY

I. Principle

The affinity of the products of the Examples for angiotensin II receptors is evaluated by the technique of displacing a radioligand specifically bound to rat adrenal angiotensin II receptors.

II. Procedure

An aliquot of a rat adrenal gland homogenate incubates in the presence of a single concentration of [$^{125}$I]-SIAII (Sar$^1$,Tyr$^4$,Ile$^8$-angiotensin II), which is an angiotensin II receptor antagonist, and two concentrations of competing agents (10$^{-5}$M, 10$^{-7}$M) for 60 min at 25° C.

The reaction is completed by the addition of a buffer, followed by rapid filtration through glass paper filters. The non-specific binding is determined in the presence of angiotensin II.

III. Expression of the Results

The results are expressed, for the concentrations tested, as the percentage displacement of the radioligand specifically bound to the adrenal angiotensin II receptors.

IV. Results

| Product of | % displacement of the labeled ligand | |
| --- | --- | --- |
|  | 1E-5M | 1E-7M |
| Example 23 | 65 | 39 |
| Example 24 | 65 | 52 |
| Example 25 | 70 | 51 |
| Example 26 | 68 | 40 |
| Example 27 | 68 | 38 |
| Example 28 | 65 | 21 |
| Example 29 | 72 | 48 |
| Example 30 | 64 | 46 |

TOXICOLOGY

The products of the Examples described have an excellent tolerance after oral administration.

Their 50% lethal dose in rats was found to be greater than 300 mg/kg.

CONCLUSION

The products of the Examples described have a good affinity for angiotensin II receptors. In this respect, they may be used beneficially for the various pathological conditions in which angiotensin II is involved, in particular for the treatment of arterial hypertension and cardiac insufficiency, in dosages of 1 to 400 mg by oral administration and of 0.01 to 50 mg by intravenous administration, in one or more dosage units per day.

What is claimed is:

1. A triazolopyrimidine compound of formula (I):

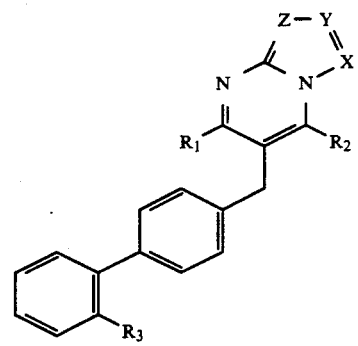

Formula (I)

in which:
one of the radicals R$_1$ and R$_2$ is a lower alkyl radical having 1 to 6 carbon atoms and the other is the hydrogen atom, a halogen atom or a group OR$_4$, SR$_4$,

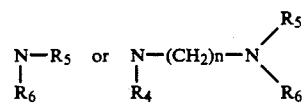

in which
R$_4$ is the hydrogen atom, a lower alkyl radical having 1 to 6 carbon atoms or a C$_3$-C$_7$ cycloalkyl radical,
R$_5$ and R$_6$, which are identical or different, are a hydrogen atom, a lower alkyl radical having 1 to 6 carbon atoms or a C$_3$-C$_7$ cycloalkyl radical, or they form, together with the nitrogen atom to which they are attached, a heterocycle selected from the group consisting of morpholine, piperazine, piperidine, pyrrolidine and imidazolidine,
n is a integer from 1 to 4,
two of X, Y and Z are the nitrogen atom and the other is a group C-R$_7$ in which R$_7$ is the hydrogen atom or a lower alkyl radical having 1 to 6 carbon atoms,
R$_3$ is a tetrazolyl group;
as well as its tautomeric form, and its pharmaceutically acceptable addition salts.

2. A compound according to claim 1 which is: 7-hydroxy-5-propyl-6[(2′-(1H-tetrazol-5-yl)biphenyl-4-yl)methyl]-1,2,4-triazolo[1,5-a]pyrimidine.

3. A compound according to claim 1 wherein R$_1$ is an n-propyl group.

4. A compound according to claim 1, wherein R$_2$ is a hydroxyl group, a morpholino group or a morpholinoethylamino group.

5. A compound according to claim 1 wherein X is the nitrogen atom.

6. A compound according to claim 1 wherein Y is the nitrogen atom or a C—CH$_3$ group.

7. A compound according to claim 1 wherein Z is the nitrogen atom or a CH group.

8. A compound according to claim 1 wherein R$_3$ is a tetrazol-5-yl group.

9. A method for the treatment of cardiovascular diseases for mammals, which comprises administering to this mammal, a therapeutically effective amount of one compound of formula (I) as defined in claim 1, or one of its pharmaceutically acceptable addition salts.

10. A pharmaceutical composition which comprises a pharmaceutically effective amount of at least one compound of the formula (I) as defined in claim 1 or one of its pharmaceutically acceptable addition salts, optionally incorporated in a pharmaceutical acceptable excipient, vehicle or carrier.

* * * * *